United States Patent [19]

Field et al.

[11] 4,256,637
[45] Mar. 17, 1981

[54] INTERMEDIATES FOR THE PRODUCTION OF IMIDAZOBENZODIAZEPINES

[75] Inventors: George F. Field, West Caldwell; William J. Zally, Creskill, both of N.J.

[73] Assignee: Hoffmann-La Roche Inc., Nutley, N.J.

[21] Appl. No.: 166,716

[22] Filed: Jul. 7, 1980

Related U.S. Application Data

[62] Division of Ser. No. 105,823, Dec. 20, 1979.

[51] Int. Cl.³ .................................................. C07D 243/16
[52] U.S. Cl. .................................................. 260/239 BD
[58] Field of Search .................................. 260/239 BD

[56] References Cited

U.S. PATENT DOCUMENTS

| | | | |
|---|---|---|---|
| 4,166,185 | 8/1979 | Walser et al. | 260/245.6 |
| 4,170,649 | 10/1979 | Liepmann et al. | 424/244 |

FOREIGN PATENT DOCUMENTS 2540522  4/1976  Fed. Rep. of Germany ........... 548/302

*Primary Examiner*—Alton D. Rollins
*Attorney, Agent, or Firm*—Jon S. Saxe; Bernard S. Leon; Frank P. Hoffman

[57] ABSTRACT

Novel intermediates of the formula

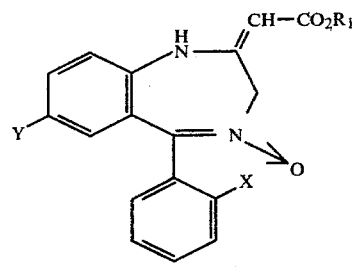

wherein X and Y are hydrogen, halogen or trifluoromethyl and $R_1$ is hydrogen or lower alkyl are presented.

Also disclosed is a process leading to the intermediates and their conversion to imidazobenzodiazepines, compounds of pharmacological activity.

1 Claim, No Drawings

INTERMEDIATES FOR THE PRODUCTION OF IMIDAZOBENZODIAZEPINES

This is a division of application Ser. No. 105,823, filed Dec. 20, 1979.

DESCRIPTION OF THE INVENTION

The present invention relates to novel intermediates of the formula

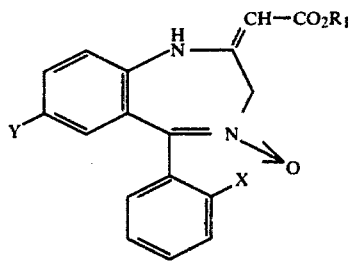

wherein X and Y are selected from the group consisting of hydrogen, halogen and trifluoromethyl and $R_1$ is hydrogen or lower alkyl.

As utilized herein the term "halogen" shall mean all four forms thereof, i.e., chloro, bromo, iodo and fluoro.

As utilized herein the term "lower alkyl" shall mean straight or branched chain hydrocarbon radicals of $C_1$ to $C_7$ length, preferably $C_1$ to $C_4$, e.g., methyl, ethyl, isopropyl, butyl, etc.

The novel intermediates and process of the present invention are illustrated in the following reaction scheme:

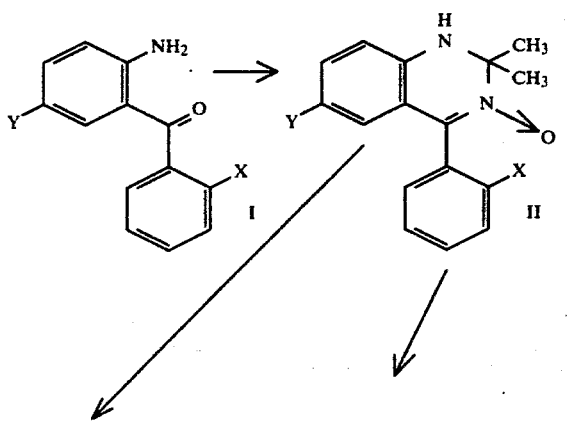

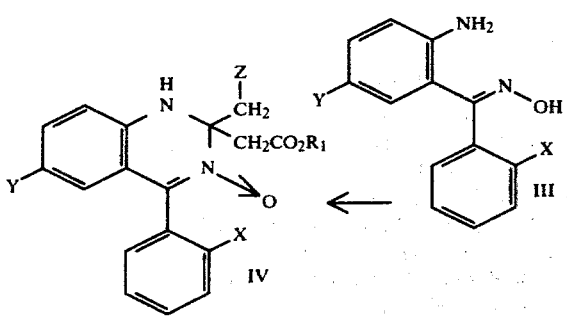

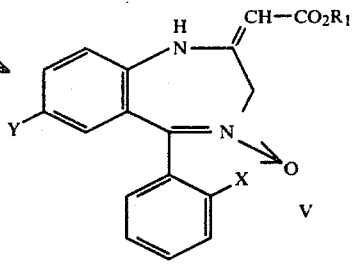

wherein X and Y are as above, Z is halogen or a leaving group and $R_1$ is lower alkyl or hydrogen.

I→II

The starting material (ketone) of formula I is a known compound, see, for example, U.S. Pat. No. 3,141,890 wherein the compound is disclosed.

The starting material is reacted with a hydroxylamine salt, such as, hydroxylamine sulfate or hydrochloride in an inert hydrocarbon solvent, such as, a $C_1$ to $C_6$ alcohol or pyridine. The reaction temperature may be varied from about 0° C. to about 200° C. with reflux temperature of the selected solvent as preferred.

Thereafter the resultant product is reacted with a lower alkyl ketone, such as, acetone, dimethyl ketone or diethyl ketone in the presence of a copper salt such as cupric sulfate or acetate or cuprous chloride. The reaction solvent can be the lower alkyl ketone itself or inert hydrocarbon solvents such as methylene chloride, benzene, toluene or a $C_1$ to $C_6$ alcohol. The reaction temperature may range from about room temperature to reflux temperature with about 60° C. as preferred.

II→III

The dihydroquinazoline compound of formula II may thereafter be reacted with water in the presence of a dilute strong acid, such as, hydrochloric, sulfuric, phosphoric or trifluoracetic acid to produce the β-oxime. The reaction may be carried out at from about 0° C. to about 80° C. with about room temperature as preferred. The compounds of formulas II and III are known compounds, see, for examle, U.S. Pat. Nos. 3,509,145; 3,505,975 and 3,398,139 and articles in the Journal of Organic Chemistry, Vol. 30, 3959 (1965) and Journal of the American Chemical Society, Vol. 89, 332 (1967).

II OR III→IV

The compounds of formulas II or III may thereafter undergo an acid catalyzed reaction with a compound of the formula

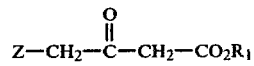

wherein $R_1$ is hydrogen or lower alkyl and Z is halogen or a leaving group.

Suitable leaving groups include aryl or alkyl sulfonyl radicals, such as, mesyl or tosyl.

Solvents suitable for the above reaction include inert organic solvents, such as, $C_1$ to $C_6$ alcohols, tetrahydrofuran and dimethylformamide. Reaction temperatures may range from about room temperature to about 120°

C. with reflux temperature of the particular solvent preferred.

IV→V

The quinazoline of formula IV is thereafter treated with a strong base, such as, an alkali metal hydroxide, alkoxide or amide, e.g., potassium or sodium hydroxide, potassium or sodium butoxide or sodium amide. Suitable solvents include inert organic solvents, such as, tetrahydrofuran, $C_1$ to $C_6$ alcohols, dimethylformamide or dimethylsulfoxide. Reaction temperatures may range from about −10° C. to about 100° C. with room temperature as preferred.

The compound of formula V is an intermediate in the preparation of imidazobenzodiazepines. Examples 13 to 23 in the present specification set forth a method of preparing such imidazobenzodiazepines which are useful as sedatives, anxiolytics, muscle relaxants and anticonvulsants but are not a part of the present invention.

The present process provides a method utilizing well-known and inexpensive starting materials and thus is less costly than prior art processes. The process steps are simple to carry out and thus require no special equipment.

EXAMPLE 1

6-Chloro-2,2-dimethyl-4-(2-fluorophenyl)-1,2-dihydroquinazoline, 3-oxide

A mixture of 25 g. (0.1 mole) of 2-amino-5-chloro-2'-fluorobenzophenone, 69.5 g. (1 mole) of hydroxylamine hydrochloride and 1 l. of pyridine was stirred and heated overnight under reflux, and then concentrated in vacuo. The residue was dissolved in ether and 10% sodium carbonate solution. The organic phase was separated, washed with water three times and with brine, dried over sodium sulfate and concentrated in vacuo to give 24 g. of an oil (crude oxime). A mixture of 24.0 g. of this oil, 2.0 g. of anhydrous $CuSO_4$ and 250 ml. of acetone was heated and stirred under reflux for 18 hours. The mixture was concentrated to dryness and the residue was partitioned between $CH_2Cl_2/H_2O$. The $CH_2Cl_2$ was washed with $H_2O$ (3x), dried over $Na_2SO_4$, filtered and concentrated in vacuo to give a crystalline residue. The residue was collected from $Et_2O$, mp 162°–165°. Recrystallization from aqueous MeOH gave yellow prisms, mp 163°–165°.

EXAMPLE 2

2-Amino-5-chloro-2'-fluorobenzophenone β-oxime

A mixture of 94.0 g. (0.308 mole) of 6-chloro-2,2-dimethyl-4-(2-fluorophenyl)-1,2-dihydroquinazoline, 3-oxide, and 2.3 l. of 3 N hydrochloric acid was stirred at room temperature for 3 hours. The solid was collected and then suspended in water. This suspension was neutralized with sodium carbonate and extracted with methylene chloride. Concentration of the extracts left crude end product as a yellowish oil. TLC indicated a 9:1 mixture of oxime and unreacted quinazoline. It was used as is in the subsequent reactions.

EXAMPLE 3

2-(Bromomethyl)-6-chloro-4-(2-fluorophenyl)-1,2-dihydroquinazoline-2-acetic acid ethyl ester 3-oxide A solution of 17.5 g. (0.07 moles) of the product of Example 2, 48.1 g. of crude ethyl 4-bromoacetoacetate in 50 ml. of EtOH and 250 ml. of ethanol containing a few drops of 3 N aqueous HCl was boiled on a steambath for ¼ hour, cooled and concentrated to a small volume. The residual mixture was partitioned between $CH_2Cl_2$ and $H_2O$. The $CH_2Cl_2$ was dried over $Na_2SO_4$, filtered and concentrated in vacuo giving an amber oil. The oil was crystallized from $Et_2O$/hexane giving crude product, mp 105°–108° (dec.). Recrystallization from EtOAc/hexane gave yellow prisms, mp 115°–117° (dec.).

EXAMPLE 4

2-(Bromomethyl)-6-chloro-4-(2-fluorophenyl)-1,2-dihydroquinazoline-2-acetic acid methyl ester, 3-oxide A solution of 3.0 g. (0.01 moles) of 6-chloro-2,2-dimethyl-4-(2-fluorophenyl)-1,2-dihydroquinazoline, 3-oxide, 3.9 g. (0.02 moles) of methyl 4-bromoacetoacetate and 100 ml. of MeOH containing a few drops of 3 N aqueous HCl was boiled for 2 hours. The mixture was diluted with several volumes of $H_2O$ and extracted with $CH_2Cl_2$ (2 x). The $CH_2Cl_2$ was dried over $Na_2SO_4$, filtered and concentrated in vacuo to give an oil. The oil was crystallized from $Et_2O$/hexane to afford yellow prisms, mp 129°–133° (dec.). Recrystallization from $CH_2Cl_2$/hexane gave yellow prisms, mp 132°–133° (dec.).

EXAMPLE 5

6-Chloro-2-(bromomethyl)-4-phenyl-1,2-dihydro-2-quinazolineacetic acid, ethyl ester, 3-oxide A solution of 123.3 g. (0.52 moles) of 2-amino-5-chlorobenzophenone (β-oxime) 250 g. (1.2 moles) of crude ethyl 4-bromoacetoacetate in 250 ml. of $Et_2O$ and 1.0 l. of EtOH was heated on a steambath for 1.4 hours. The solution was chilled on ice and the crystals collected to give yellow prisms, mp 133°–135° (dec.). Recrystallization from $CH_2Cl_2$/hexane afforded pure yellow prisms, mp 133°–135° (dec.).

EXAMPLE 6

2-(Bromomethyl)-6-chloro-4-phenyl-1,2-dihydroquinazoline-2-acetic acid methyl ester, 3-oxide A solution of 6.2 g. (0.025 moles) of 2-amino-5-chlorobenzophenone (β-oxime), 5.9 g. (0.030 moles) of methyl 4-bromoacetoacetate and 100 ml. of MeOH containing a few drops of 3 N aqueous HCl was boiled for ¼ hour. The solution was cooled, diluted with several volumes of $H_2O$ and extracted with $CH_2Cl_2$. The $CH_2Cl_2$ extract was dried over $Na_2SO_4$, filtered and concentrated in vacuo to give an oil. The oil was crystallized from $Et_2O$/hexane giving yellow prisms, mp 135°–138° (dec.). Recrystallization from EtOAc gave yellow prisms, mp 137°–138° (dec.).

EXAMPLE 7

6-Chloro-2-(chloromethyl)-4-phenyl-1,2-dihydro-2-quinazoline acetic acid, ethyl ester, 3-oxide A mixture of 7.4 g. (0.03 moles) of 2-amino-5-chlorobenzophenone, 5.2 g. (0.033 moles) of ethyl 4-chloroacetoacetate and 75 ml. of EtOH containing 3 drops of 3 N aqueous HCl was heated on a steambath for 20 minutes. The solution was chilled on ice and the crystals collected to give crude product, mp 140°–142° (dec.). Recrystallization from EtOH afforded yellow prisms, mp 143°–145° (dec.).

EXAMPLE 8

7-Chloro-5-(2-fluorophenyl)-1,2-dihydro-3H-1,4-benzodiazepine-2-ylidene acetic acid ethyl ester, 4-oxide To a solution of 4.5 g. (0.01 mole) of the end product of Example 3 in 100 ml. of ethanol was added 1.3 g. (0.012 mole) of potassium t-butoxide. The solution was stirred at room temperature overnight and then concentrated in vacuo. The residue was partitioned between methylene chloride and water. The organic layer was washed with water, dried over sodium sulfate and concentrated in vacuo. The residue was slurried with ether to give end product, mp 145°–150°. Recrystallization from ethyl acetate/hexane gave off-white prisms, mp 148°–150° (dec.).

EXAMPLE 9

7-Chloro-5-(2-fluorophenyl)-1,2-dihydro-3H-1,4-benzodiazepin--ylidene acetic acid methyl ester, 4-oxide To a stirred solution of 2.2 g. (0.05 moles) of the end product of Example 4 in 100 ml. of MeOH 0.54 g. (0.01 moles) of NaOCH$_3$ was added. After ¾ hour, the solution was diluted with H$_2$O and extracted with CH$_2$Cl$_2$. After drying and evaporation, an oil was obtained. The oil was taken up CH$_2$Cl$_2$ and filtered through a plug of silica gel eluting with CH$_2$Cl$_2$. The eluates were concentrated to dryness and the residue slurried with Et$_2$O to give analytically pure product as off-white prisms, mp 192°–193° (dec.).

EXAMPLE 10

7-Chloro-5-phenyl-2,3-dihydro-1H-benzodiazepin-1,4-2-ylidene acetic acid, ethyl ester, 4-oxide To a solution of 1.3 g. (12 mmol) of potassium t-butoxide in 100 ml. of ethanol cooled to 5° was added 4.4 g. (10 mmole) of the end product of Example 5. The ice bath was removed and the reaction mixture was stirred for 1.5 hours while coming to room temperature. After concentration in vacuo it was diluted with water, the pH was adjusted to 7 by addition of acetic acid, and it was extracted with methylene chloride. The organic phase was washed with water, dried over sodium sulfate and concentrated in vacuo to leave 3.5 of tacky solid. This was slurried with ether to give crude product; mp 136°–138°. Recrystallization from ethyl acetate/hexane gave off-white prisms, mp 138°–140°.

EXAMPLE 11

7-Chloro-5-phenyl-2,3-dihydro-1H-1,4-benzodiazepin-3-ylidene acetic acid ethyl ester, 4-oxide From 13.1 g. (30 mmole) of the end product of Example 5 treated with potassium t-butoxide as above, there was obtained an oil, which showed two spots on TLC. This oil was chromatographed on 175 g. of silica gel. Elution with ethyl acetate gave the end product of Example 10, mp 137°–140°. Elution with ethanol gave the desired end product after crystallization from ether. Recrystallization from ethanol gave yellow prisms, mp 186°–188°.

EXAMPLE 12

Conversion of 2-amino-5-chlorobenzophenone to 7-chloro-5-phenyl-2,3-dihydro-1H-benzodiazepin-1,4,-2-ylidene acetic acid, ethyl ester, 4-oxide A mixture of 7.4 g. (30 mmole) of 2-amino-5-chlorobenzophenone (β-oxime), 5.2 g. (33 mmole) of ethyl 4-chloroacetoacetate, 125 ml. of ethanol and 4 drops of 3 N hydrochloric acid was heated under reflux with stirring for 0.5 hour. It was then cooled to 10° in an ice bath, and with stirring 60 ml. of 1 N sodium hydroxide was added. After 0.5 hour, a white solid had precipitated. The reaction mixture was diluted with water and acidified to pH 6 with 3 N hydrochloric acid. The solid was collected and washed with water to give the end product; mp 140°–142° (dec.).

EXAMPLE 13

7-Chloro-5-(2-fluorophenyl)-1,3-dihydro-2H-1,4-benzodiazepine-2-ylideneacetic acid ethyl ester Phosphorous trichloride, 10 ml., was added to a solution of 10 g. (0.0266 mol) of 7-chloro-5-(2-fluorophenyl)-1,3-dihydro-2H-1,4-benzodiazepine-4-oxide-2-ylideneacetic acid ethyl ester in 100 ml. of methylene chloride. After standing at room temperature for 3 hours, the reaction mixture was washed with 10% aqueous sodium carbonate solution. The methylene chloride layer was separated, dried over sodium sulfate and evaporated. This crude material was directly used for the next step. For the purpose of characterization a sample was purified by filtering over a pad of silica gel using 10% of ethyl acetate in methylene chloride. Crystallization from ethanol gave colorless crystals with mp 109°–111°.

EXAMPLE 14

7-Chloro-5-(2-chlorophenyl)-1,3-dihydro-2H-1,4-benzodiazepine-2-ylideneacetic acid ethyl ester Phosphorus trichloride, 5 ml., was added to a solution of 7.8 g. (0.02 mol) of 7-chloro-5-(2-chlorophenyl)-1,3-dihydro-2H-1,4-benzodiazepine-4-oxide-2-ylideneacetic acid ethyl ester in 100 ml. of methylene chloride. After stirring at room temperature for 1½ hours, the solvent was evaporated under reduced pressure, at the end azeotropically with toluene. The residue was partitioned between methylene chloride and 10% aqueous sodium carbonate solution. The organic layer was dried and evaporated to yield crude product which partially crystallized from 2-propanol. A portion of these crystals, 0.5 g., was recrystallized from methylene chloride/ethanol for analysis to give off-white crystals with mp 103°–105°.

EXAMPLE 15

In the same fashion as Example 14 were prepared:

7-Chloro-5-(2-fluorophenyl)-1,3-dihydro-2H-1,4-benzodiazepine-2-ylideneacetic acid isopropyl ester.

Crystallized from 2-propanol, mp 144°–145°.

7-Chloro-5-(2-fluorophenyl)-1,3-dihydro-2H-1,4-benzodiazepine-2-ylideneacetic acid tert. butyl ester Crystallized from hexane, mp 158°–160°.

EXAMPLE 16

7-Chloro-5-(2-fluorophenyl)-alpha-hydroxyimino-3H-1,4-benzodiazepine-2-acetic acid ethyl ester.

The crude 7-chloro-5-(2-fluorophenyl)-1,3-dihydro-2H-1,4-benzodiazepine-2-ylideneacetic acid ethyl ester obtained by reduction of 10 g. of the end produce of Example 15 as described above was dissolved in 40 ml. of glacial acetic acid. Sodium nitrite, 2.45 g., was added with stirring over a period of 5 minutes. Following the addition the mixture was stirred at room temperature for 15 minutes. The product started to crystallize and was further precipitated by addition of 50 ml. of water. The crystals were collected, washed with water, ethanol and ether to yield the end product. The analytical sample was recrystallized from tetrahydrofuran/ethanol to give pale yellow crystals with mp 230°–233°.

EXAMPLE 17

7-Chloro-5-(2-chlorophenyl)-alpha-hydroxyimino-3H-1,4-benzodiazepine-2-acetic acid ethyl ester.

Sodium nitrite, 1.5 g. (0.022 mol), was added to a solution of 6.2 g. crude 7-chloro-5-(2-chlorophenyl)-1,3-dihydro-2H-1,4-benzodiazepine-2-ylideneacetic acid ethyl ester in 75 ml. of glacial acetic acid. After stirring at room temperature for 20 minutes the reaction mixture was diluted with 200 ml. of water. The precipitated product was collected, washed with water and sucked dry to give crude product. The analytical sample was recrystallized from methylene chloride/ethanol to give light yellow crystals with mp 219°–221°.

EXAMPLE 18

Similarly as in Example 17 there were obtained:

7-Chloro-5-(2-fluorophenyl)-alpha-hydroxyimino-3H-1,4-benzodiazepine-2-acetic acid isopropyl ester.

Crystallized from tetrahydrofuran/2-propanol, mp 244°–245° dec.

7-Chloro-5-(2-fluorophenyl)-alpha-hydroxyimino-3H-1,4-benzodiazepine-2-acetic acid tert.butyl ester.

Crystallized from methylene chloride/hexane, mp 212°–214°.

EXAMPLE 19

8-Chloro-6-(2-fluorophenyl)-1-methyl-4H-imidazo[1,5-a][1,4]benzodiazepine-3-carboxylic acid, ethyl ester (A) Phosphorus trichloride, 1 ml., was added to a solution of 1 g. (2.4 mmol) of 8-chloro-6-(2-fluorophenyl)-1-methyl-4H-imidazo[1,5-a][1,4]benzodiazepine-5-oxide-3-carboxylic acid, ethyl ester in 25 ml. of methylene chloride. After standing at room temperature for 2 days, the solution was washed with 10% aqueous sodium carbonate solution, dried over sodium sulfate and evaporated. Crystallization of the residue from ether gave end product with mp 174°–176°.

(B) A mixture of 0.5 g. (1.24 mmol) of 7-chloro-5-(2-fluorophenyl)-alpha-hydroxyimino-3H-1,4-benzodiazepine-4-oxide-5-acetic acid ethyl ester 30 ml. of tetrahydrofuran, 10 ml. of ethanol and 0.25 g. of 10% palladium on carbon was hydrogenated at atmospheric pressure for 3 hours. A solution of acetaldehyde in tetrahydrofuran (10% v/v) was then added in three portions of 0.2 ml. at 1 hour intervals. After a total reaction time of 6 hours the catalyst was filtered off and the filtrate was evaporated. The residue was chromatographed over 7 g. of silica gel using methylene chloride/ethyl acetate 1:1. Crystallization of the clean fractions from ether gave end product with mp 196°–198° after recrystallization from ethyl acetate/hexane.

EXAMPLE 20

8-Chloro-6-(2-fluorophenyl)-1-methyl-4H-imidazo[1,5-a][1,4]benzodiazepine-3-carboxylic acid, isopropyl ester (A) A mixture of 2 g. (5 mmol) of 7-chloro-5-(2-fluorophenyl)-alpha-hydroxyimino-3H-1,4-benzodiazepine-2-acetic acid isopropyl ester, 50 ml. of tetrahydrofuran, 15 ml. of 2-propanol, 3 g. of Raney nickel and 0.5 ml. of methanol containing 20% (v/v) of ammonia was hydrogenated at atmospheric pressure for 4 hours. The catalyst was filtered off and the filtrate was evaporated. The residue was dissolved in 50 ml. of methylene chloride and treated with 0.6 ml of acetaldehyde. After stirring at room temperature for 30 minutes 2 g. of activated manganese dioxide was added and stirring was continued for another half hour. The $MnO_2$ was separated by filtration over Celite and the filtrate was evaporated. Crystallization of the residue from ether gave end product in two crops. For analysis it was recrystallized from ethyl acetate, mp 200°–202°.

(B) This compound was also obtained by treatment of the corresponding N-oxide with phosphorus trichloride.

EXAMPLE 21

8-Chloro-6-(2-fluorophenyl)-1-methyl-4H-imidazo[1,5-a][1,4]benzodiazepine-3-carboxylic acid tert.butyl ester The product was obtained by hydrogenation of 7-chloro-5-(2-fluorophenyl)-alpha-hydroxyimino-3H-1,4-benzodiazepine-2-acetic acid tert.butyl ester followed by oxidative condensation with acetaldehyde. It was crystallized from methylene chloride/hexane to give colorless crystals with mp 215°–217°.

EXAMPLE 22

8-Chloro-6-(2-fluorophenyl)-1-methyl-4H-imidazo[1,5-a][1,4]benzodiazepine-3-carboxylic acid (A) A mixture of 0.15 g. (0.39 mmol) of 8-chloro-6-(2-fluorophenyl)-1-methyl-4H-imidazo[1,5-a][1,4]benzodiazepine-5-oxide-3-carboxylic acid, 0.75 ml. of phosphorus trichloride and 25 ml. of methylene chloride was stirred at room temperature for 24 hours. The solvent was removed under reduced pressure and the residue was dissolved in 1 N sodium hydroxide solution. The solution was then acidified with glacial acetic acid and extracted with methylene chloride. The extracts were dried and evaporated and the residue was crystallized from methanol/ethyl acetate to yield colorless crystals with mp 272°–274° dec. (AW 7047/118)

(B) This compound was also obtained by alkaline hydrolysis of the ethyl ester of Example 19.

(C) This acid can also be prepared by alkaline hydrolysis of the isopropyl ester of Example 20 or by cleavage of the tert.butyl ester of Example 21 with trifluoroacetic acid.

What is claimed:

1. A process to produce a compound of the formula

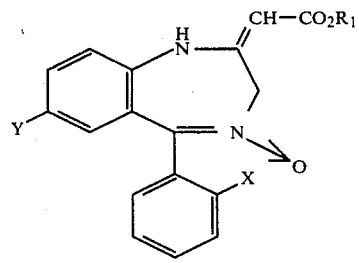

wherein X and Y are selected from the group consisting of hydrogen, halogen and trifluoromethyl and $R_1$ is hydrogen or lower alkyl which comprises:

(A) reacting a compound of the formula

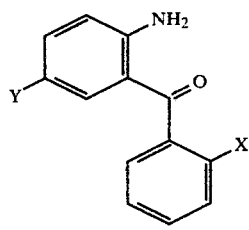

wherein X and Y are as above with a hydroxylamine salt at from 0° C. to about 200° C. and thereafter reacting the resultant product with a lower alkyl ketone in the presence of a copper salt at from about room temperature to reflux temperature (B) reacting the product of (A) with water in the presence of a dilute strong acid at from about 0° C. to about 80° C.

(C) reacting the product (A) or (B) with a compound of the formula

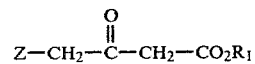

wherein $R_1$ is as above and Z is a suitable leaving group at from about room temperature to about 120° C. and (D) reacting the product of (C) with a base at from about −10° C. to about 100° C.

* * * * *